(12) United States Patent
Selvin et al.

(10) Patent No.: US 9,012,870 B2
(45) Date of Patent: Apr. 21, 2015

(54) TWO-PHOTON 3-D FIONA OF INDIVIDUAL QUANTUM DOTS

(71) Applicants: Paul R. Selvin, Urbana, IL (US); Ruobing Zhang, Williamstown, MA (US); Eli Rothenberg, New York, NY (US)

(72) Inventors: Paul R. Selvin, Urbana, IL (US); Ruobing Zhang, Williamstown, MA (US); Eli Rothenberg, New York, NY (US)

(73) Assignee: Board of Trustees of the University of Illinois, Urbana, IL (US)

( * ) Notice: Subject to any disclaimer, the term of this patent is extended or adjusted under 35 U.S.C. 154(b) by 13 days.

(21) Appl. No.: 13/949,221

(22) Filed: Jul. 23, 2013

(65) Prior Publication Data

US 2014/0021371 A1    Jan. 23, 2014

Related U.S. Application Data

(60) Provisional application No. 61/674,406, filed on Jul. 23, 2012.

(51) Int. Cl.
*G01N 21/64* (2006.01)

(52) U.S. Cl.
CPC ............ *G01N 21/64* (2013.01); *G01N 21/6458* (2013.01)

(58) Field of Classification Search
CPC .............. G01N 21/64; G01N 21/6428; G01N 21/6458; G01N 33/582
USPC ........................................... 250/458.1, 459.1
See application file for complete search history.

(56) References Cited

U.S. PATENT DOCUMENTS

| | | | |
|---|---|---|---|
| 7,130,115 B2 * | 10/2006 | Olszak et al. ................. | 359/372 |
| 7,439,497 B2 * | 10/2008 | Dantus et al. ................. | 250/288 |
| 7,675,045 B1 * | 3/2010 | Werner et al. .............. | 250/458.1 |
| 2012/0193530 A1 * | 8/2012 | Parker et al. .................. | 250/307 |

* cited by examiner

*Primary Examiner* — Mark R Gaworecki
(74) *Attorney, Agent, or Firm* — Richard Aron Osman

(57) ABSTRACT

Microscopy is performed by imaging individual quantum dots (QD) using two-photon (2P) microscopy of in an aqueous environment with widefield and point-scan excitations at nanometer accuracy.

10 Claims, 7 Drawing Sheets

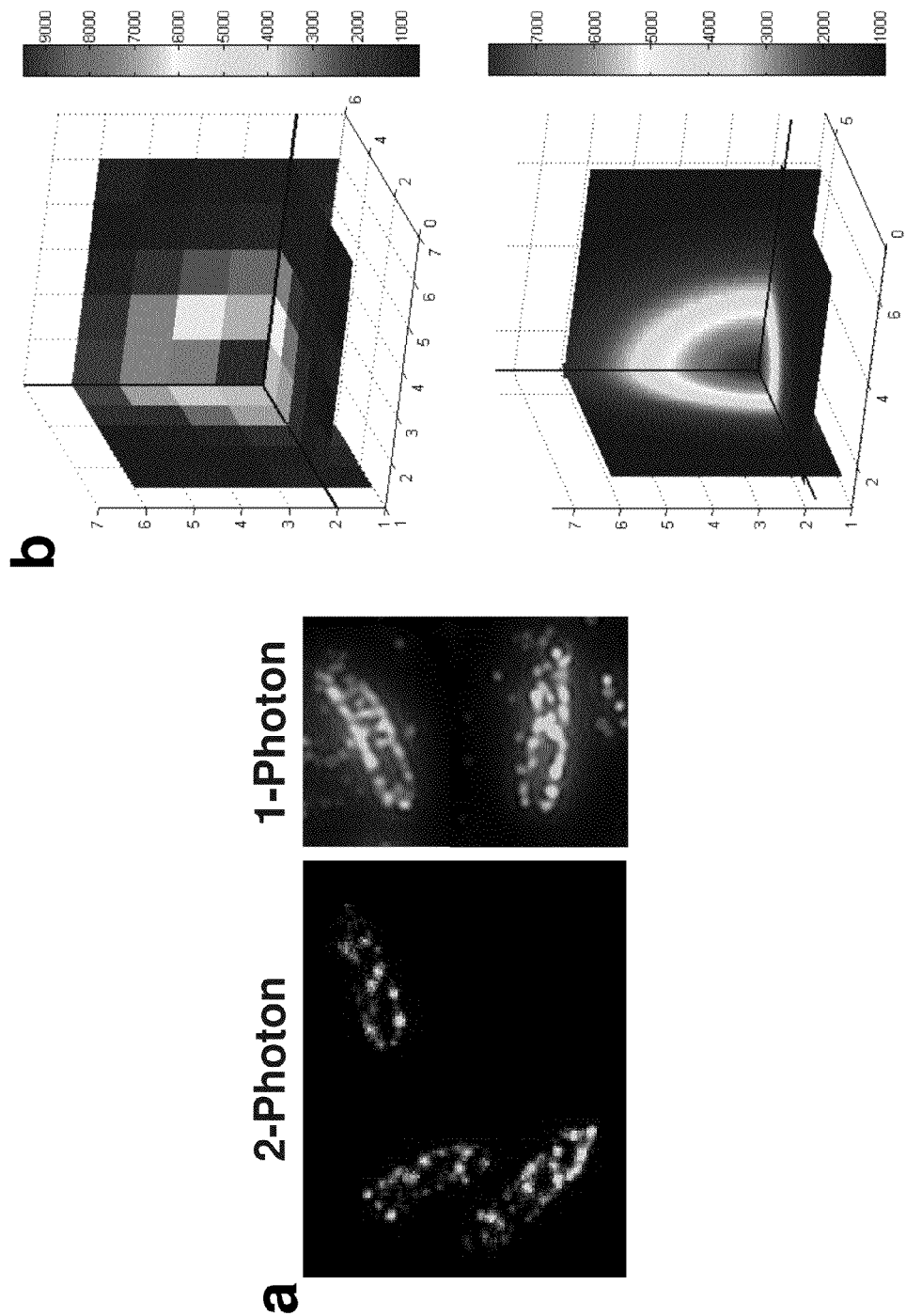
Fig. 4 (a-b)

TWO-PHOTON 3-D FIONA OF INDIVIDUAL QUANTUM DOTS

CROSS-REFERENCE TO RELATED APPLICATION

This application claims priority to U.S. Ser. No. 61/674,406 filed Jul. 23, 2012.

STATEMENT RE GOVERNMENT RIGHTS

This invention was made with government support under contract numbers GM086214 and R01GM082837 awarded by the National Institutes of Health. The government has certain rights in the invention.

INTRODUCTION

One-photon (1P) microscopy of individual quantum dots (QDs) has become routine[1,2,3]. In contrast, two-photon (2P) microscopy of individual QDs has not had the same success despite the many advantages that 2P microscopy offers: reduced scattering, deep sample penetration, and intrinsic confocality when excited with point excitation[4]. 2P microscopy of ensembles of QDs in aqueous samples has been achieved by Larson et al. in 2003[5]. They showed QDs had large absorption cross-sections under 2P scan excitation. Nevertheless, individual 2P QD-microscopy has been possible only in artificial environments, such as air-dried samples of QDs[6], or at cryogenic temperatures[7]. 2P microscopy of individual organic-based fluorophores has also been problematic since most fluorophores have very small 2P absorption cross-sections, as well as poor photostability[8,9].

Here we report the application of 2P microscopy to individual QDs in a biological setting with nanometer spatial accuracy in three dimensions, both in solution and in live and fixed cells. We call our technique Two-Photon Fluorescence Imaging with One Nanometer Accuracy (2P FIONA), in analogy with the one-photon technique[10]. With 2P excitation, we are able to achieve three-dimensional (3D) nanometer spatial accuracy, as opposed to the two-dimension FIONA previously achieved with one photon microscopy[10]. We also introduce a fast imaging method using a holographic matrix in excitation and EMCCD in detection that achieves an 80-fold improvement in speed and reduces spherical aberrations.

SUMMARY OF THE INVENTION

Two-photon (2P) microscopy of individual quantum dots (QD) in an aqueous environment with both widefield and point-scan excitations at nanometer accuracy is reported for the first time. Thiol-containing reductants suppress QD blinking and enable measurement of the 36 nm step size of individual Myosin V motors in vitro. QDs are localized with an accuracy of 2~3 nm in all three dimensions by using a 9×9 matrix excitation hologram and an array detector, which also increases the 3D scan imaging rate by 80-fold. With this 3D microscopy the LamB receptor distribution on E. coli and the endocytosis of EGFRs in breast cancer cells was validated.

The invention provides an extraordinary innovation, which culminated from years of painstaking efforts. One obstacle was that with normal 2-photon excitation of dyes, extraordinary high peaks powers are needed. (The lasers are peaked, so while the average power is not extraordinary, the peak power is; a Ti-Sapphire puts out a 150 fsec pulse every 9 nanosecond, or so. So the average power is taken and divided by 9 nsec/150 fsec=100,000 to get the peak power.) That is why Titanium-Sapphire lasers are preferred, with relatively short pulses, to keep the average power somewhat reasonable. Watt Webb reported that it was in the femtosecond range, which is what most Ti-Saph lasers put out. Stefan Hell found that you could get reasonable excitation with picosecond pulses. While we still use Ti-Sapphire lasers, one innovation we developed was to use substantially less average power than typically used with organic fluorophores—before this we typically burned out the QDs and did not obtain useful imagery.

The invention provides method, compositions and systems for two-photon fluorescence imaging with nanometer-scale accuracy. In one aspect the invention provides a method of microscopy comprising the step of imaging individual quantum dots (QD) using two-photon (2P) microscopy of in an aqueous environment with widefield and point-scan excitations at nanometer accuracy.

In various particular embodiments the method further comprises the step of:
  using a thiol-containing reductant to suppress QD blinking, particularly a small molecular weight (e.g. <250 MW) thiol like Dithiothreitol or B-mercaptoethanol;
  localizing the QDs with an accuracy of 2~3 nm in all three dimensions by using a 9×9 matrix excitation hologram and an array detector; and/or
  using a holographic matrix in excitation and an electron multiplying charge coupled device (EMCCD) in detection.

The various embodiments may be practiced wherein the imaging is performed at an ambient (room) or a cell-viability permissive temperature, and/or wherein the quantum dots are attached to a biological molecule, wherein the method images the molecule, such as wherein the molecule is present on or in a cell, such as a living mammalian or human cell.

The invention also provides systems and devices for specifically tailored to implement these methods.

The disclosure may be further understood by the following non-limiting exemplification. All references cited herein are hereby incorporated by reference to the extent not inconsistent with the disclosure herewith. Although the description herein contains many specificities, these should not be construed as limiting the scope of the disclosure but as merely providing illustrations of some of the presently preferred embodiments of the disclosure. For example, thus the scope of the disclosure should be determined by the appended claims and their equivalents, rather than by the examples given.

DETAILED DESCRIPTION OF SPECIFIC EMBODIMENTS OF THE INVENTION

Figure 1:
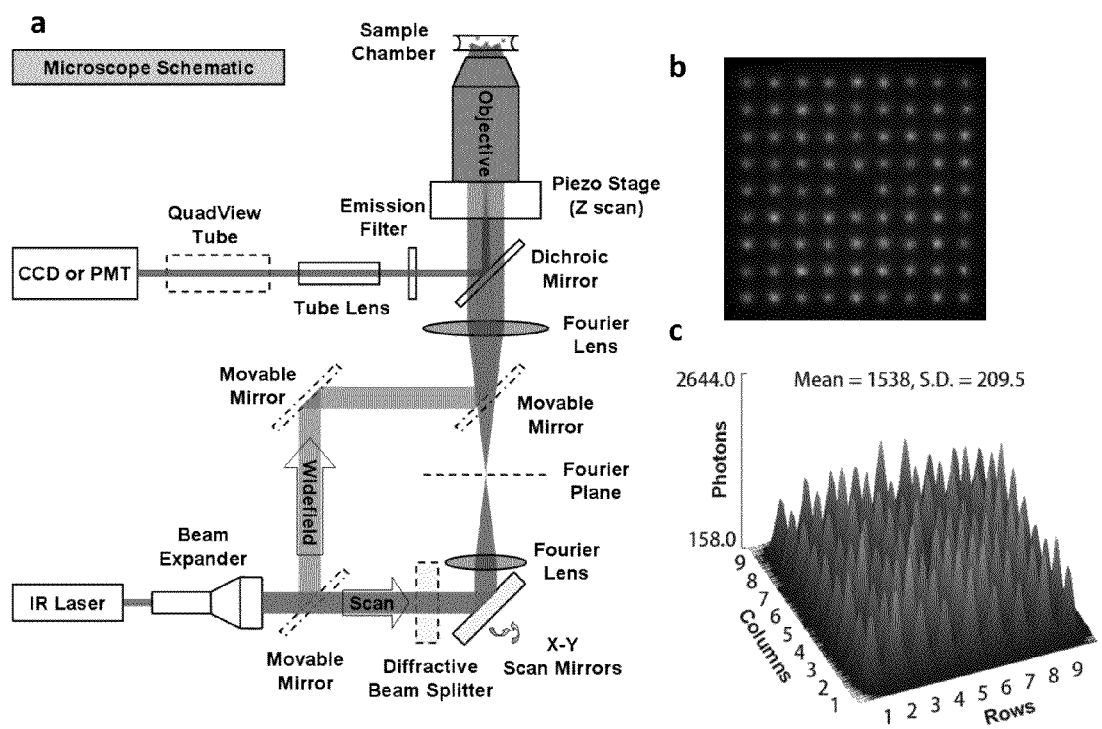
FIG. 1: Configuration of the 2P microscope. (a) Widefield and single- and multi-point scan. In the sample chamber a 3×3 matrix, instead of the actual 9×9 matrix is illustrated for clarity. The holograph splitter is conjugated via two 4f lenses to the back focal plane of the objective. (b) Image of excitation hologram matrix. Taken with 1 µM Qdot 605, laser at 785 nm. (c) 2D intensity plot of the hologram matrix in (b): SD=13.6%.
Figure 2:
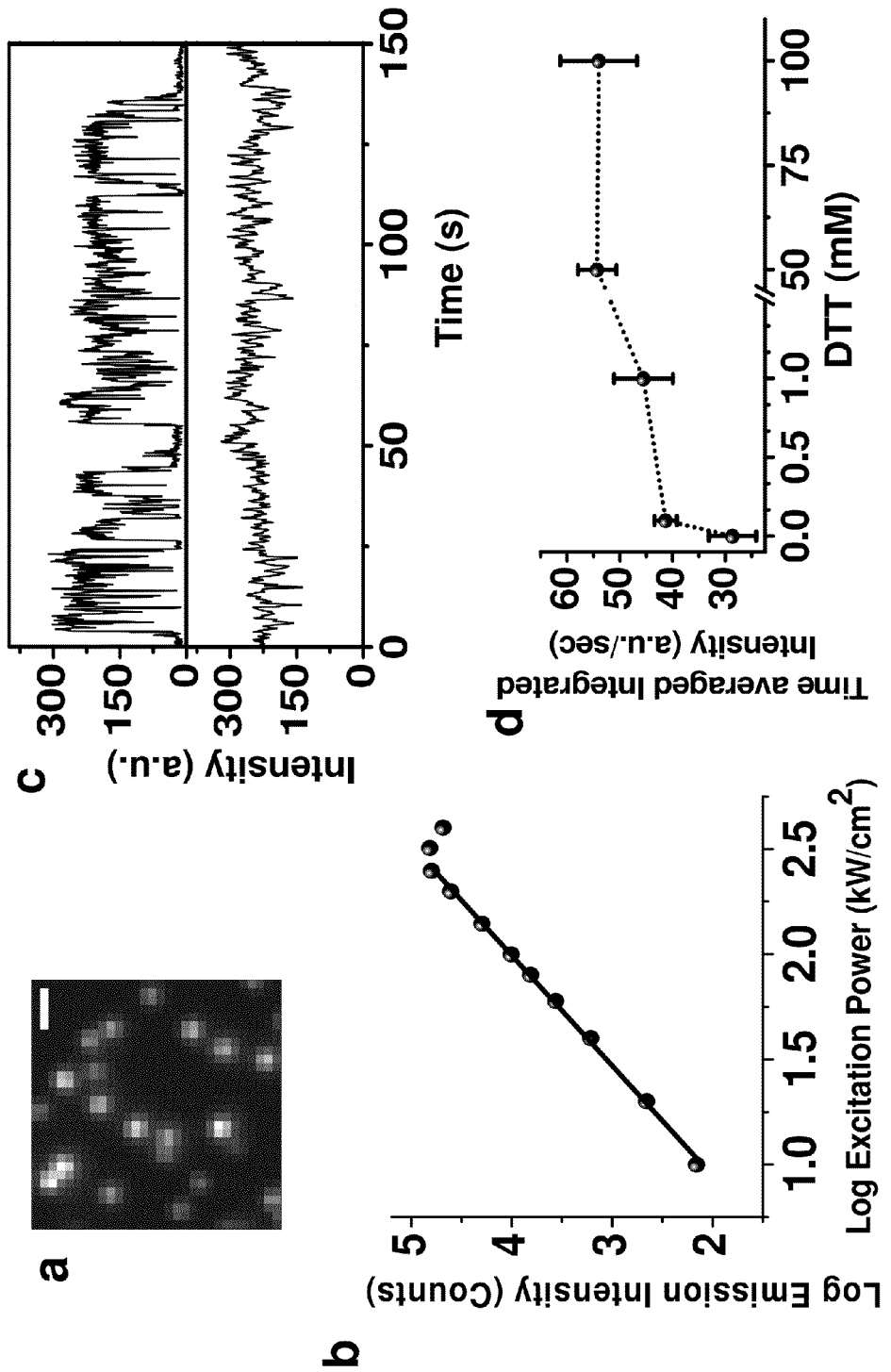
FIG. 2: Two-photon excitation response of Quantum Dots. (a) An Image of 2P excited individual QD 525. Scale bar is 500 nm. QDs were conjugated to streptavidin and tethered to a BSA-biotin coated surface. Imaging buffer (DPBS, pH 7.5) was supplemented with 50 mM DTT. (b) The log average emission intensity of individual QDs plotted versus log excitation power. Slope of linear fit is 1.93, indicating QDs have a predominant quadratic dependence of fluorescence on laser power, in agreement with quadratic power law dependence of two-photon excitation. At higher two-photon excitation power QDs emission is saturated and fast photobleaching occurs. (c) Blinking is near completely eliminated by adding in 50 mM DTT. (d) DTT enhances the QD emission more as its concentration increases.
Figure 6A:
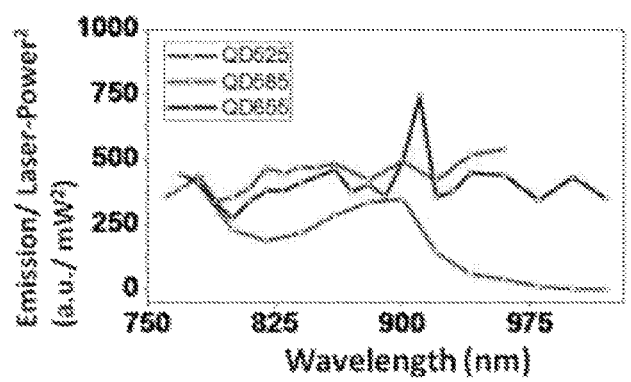
FIG. 6A. Excitation spectra of three kinds of QDs whose emission peaks are at 525 nm, 585 nm and 655 nm, respectively. For one-photon excitation, see Larson et al.

We first imaged immobilized single QDs in an aqueous buffer via a widefield 2P microscope (FIG. 1 "Widefield" path, and FIG. 2a). Ordinarily, a scanning system is used in 2P microscopy of regular organic fluorophores. However, widefield microscopy is possible with QDs because their 2P excitation is extremely efficient. The log emission intensity vs. log excitation power plot indicates the $I^2$ dependence of 2P excitation (FIG. 2b). At a 2P excitation flux of $\geq 250$ kW/cm$^2$, saturation begins to take place, accompanied by significant photobleaching. The photobleaching occurs at the power about 20 times lower than the 2P excitation levels reported for organic dyes[4,5]. Furthermore, the addition of small thiols into the buffer, as has been observed for 1P excitation[11], is very helpful. 1-100 mM Dithiothreitol (DTT; M.W.=154) or 1-10% B-Mercaptoethanol (BME; M.W.=78) results in nearly complete (>90%) suppression of blinking (FIG. 2c). Without reductants present, the QDs tend to blink extensively. However, the blinking does prove that they are single QDs. Larger molecular weight reductants (e.g. glutathione, M.W.=307) did not have this effect. FIG. 2d shows the effect of DTT on the averaged emission intensity of >100 individual QDs, where an increase in DTT concentration clearly results in an increase in average emission intensity due to suppression of blinking and elimination of non-emitting "off" states. The QDs could also be conveniently used for multi-color detection with a single 2P excitation, just as is true with 1P excitation. The excitation spectra, ranging from 760 nm to 1000 nm of three different QDs samples with peak emissions at 525 nm, 585 nm and 655 nm, displayed highly efficient excitation from 760-900 nm (FIG. 6A).

Figure 3:
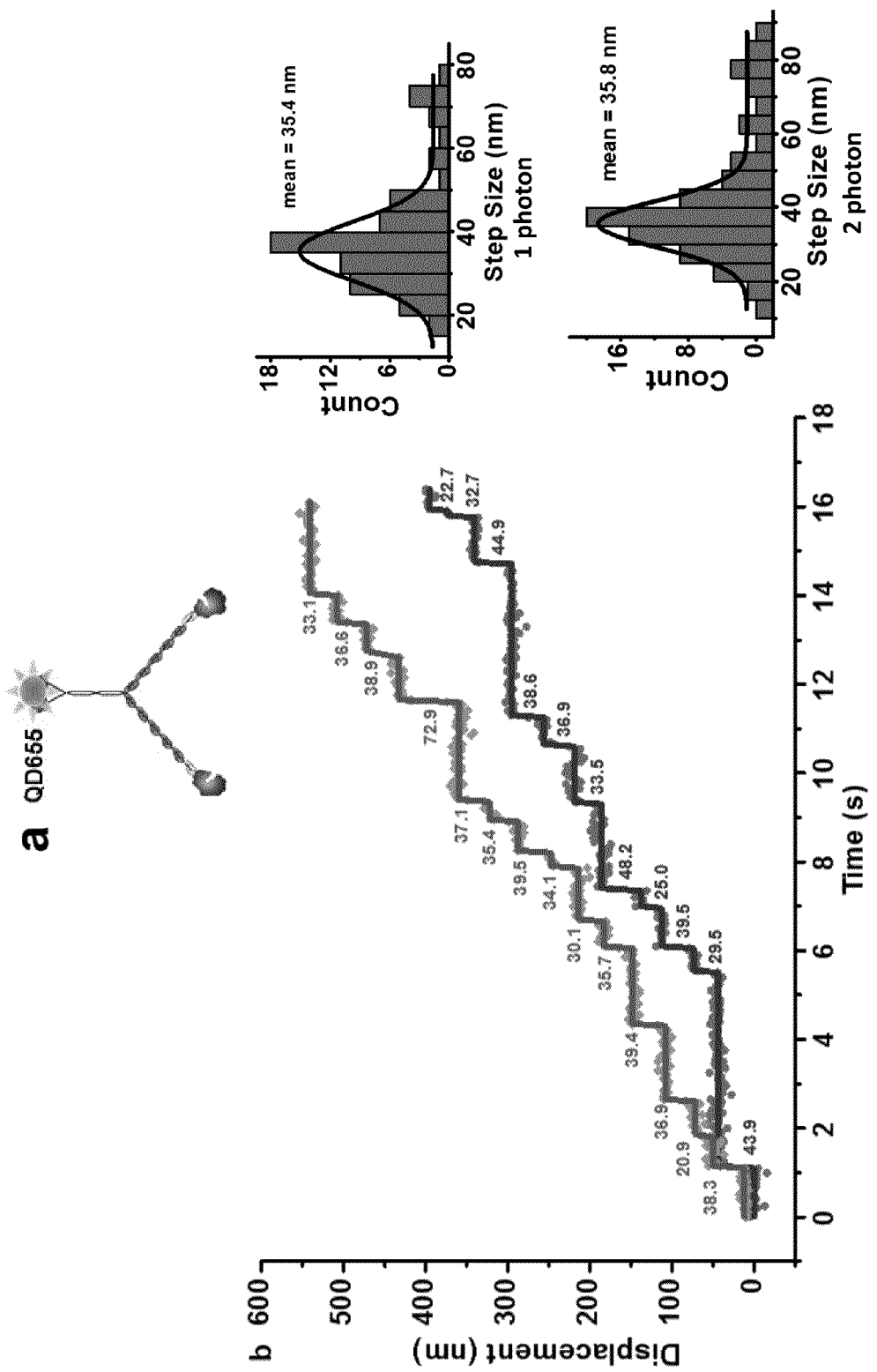
FIG. 3: 2P widefield excitation resolves Myosin V step sizes at nanometer accuracy. (a) Labeling of dimeric myosin V construct. (b) Displacements of myosin V motors resolved at 50 ms temporal and one nanometer spatial resolutions under 1P (orange dots, green lines) and 2P (red dots, blue lines) excitation. Step sizes are determined by Student's t-test, and the step size distribution is fit to a Gaussian fit to give 35.4±7.0 nm and 35.8±6.3 nm for 1P and 2P widefield imaging, respectively.

With blinking suppressed, QDs under 2P widefield excitation have continuous emission and can be used for tracking of biomolecular motion at nanometer accuracy. We have analyzed a molecular motor, a dimerized myosin V, by placing a QD (655 nm) on the C-terminus (FIG. 3a) and exciting it with either 1P or 2P widefield excitation. We expected the step size to be ~36 nm based on previous results from optical trapping[12] and 1P-FIONA data[10]. At 30 ms exposure time, under 2P widefield excitation at 200 kW/cm$^2$, we detected ~25,000 photons and achieved 0.9 nm accuracy; under 1P widefield excitation at 0.4 kW/cm$^2$, we detected ~20,000 photons and achieved 1.1 nm FIG. 3b shows myosin V walking with 2 μM ATP, integrated every 50 ms, and excited either with 1P or 2P excitation. With 1P, we measured the step size of the motor to be 35.4+/-7.0 nm; with 2P, we measured 35.8+/-6.3 nm. These results are in excellent agreement with each other and consistent with the expected value. The motor protein stepping rate is evidently not affected by the strong IR power used in 2P excitation, indicating that the laser field does not harm the ATPase activity of myosin V. We also note that total internal reflection (TIR) or near-TIR[13,14] was not required here because of the exceptional brightness and signal-to-noise of the QDs. Nevertheless, single QDs could be excited and imaged with 2P-TIR (FIG. 6B), confirming the high absorption cross-section of QDs under 2P.

Widefield illumination, however, does not give z-axis discrimination. To achieve this, we used either single-point or multiple-point scanning excitation where the beam(s) was focused to a (near) diffraction-limited focal spot(s). By adding in a holographic beam splitter (Holo/Or Ltd, Israel) into the beam path, we split the beam and generated a 9×9 matrix of 80 diffraction-limited focal spots for excitation (See "Scan" excitation path in FIG. 1; the central spot is missing, yielding 81−1=80 spots). The single- or multiple-point was raster scanned in the usual fashion—by a pair of motorized minors in x and y directions and by a piezo-stage mounted under the objective in the z-axis. We found this considerably simplified the optics compared with the moving mirrors[15,16] or rotational microlenses[17] used previously. Our system could also be easily integrated into current single-point scan microscopes, and its imaging area coverage was conveniently adjustable by changing the conjugation lenses magnification. At the sample, the 80 spots were separated 1.5 um apart with the 100× objective, and quite uniform in terms of power distribution (standard deviation is 6%), leading to very small localization accuracy errors. In most experiments, we scanned at 100 nm steps in all three dimensions. Moreover, to acquire the simultaneous emission excited by the multiple focal spots, we used an array detector, i.e. an EMCCD camera. The effective pixel size of the EMCCD after magnification was also 100 nm. This holographic matrix (HM) scan technique leads to an 80-fold improvement over single-point scan imaging speed (assuming, of course, that you are imaging the area covered by the matrix). Furthermore, given the brightness of QDs under 2P excitation, the imaging time is also relatively fast. In our cell imaging experiments (see below), for example, a 3D scan requires only 1~3 seconds or even sub-second depending on the scan step dwell time, while the traditional single-point 2P scan microscope based on organic fluorophores often takes tens of minutes. For example, we applied 3D scanning microscopy to live E. coli cells, of which the LamB receptors (binding targets of bacteriophage) were labeled with QD 605 (FIG. 4a)[18,19]. E. coli cells' viability was not perturbed by the 2P excitation as evidenced by the division of some cells after imaging. The image revealed spatial helices or bands of the receptors on the E. coli membrane. Breast cancer cell, another example of the multi-point scanning (FIG. 4c), is discussed below.

Figure 4:
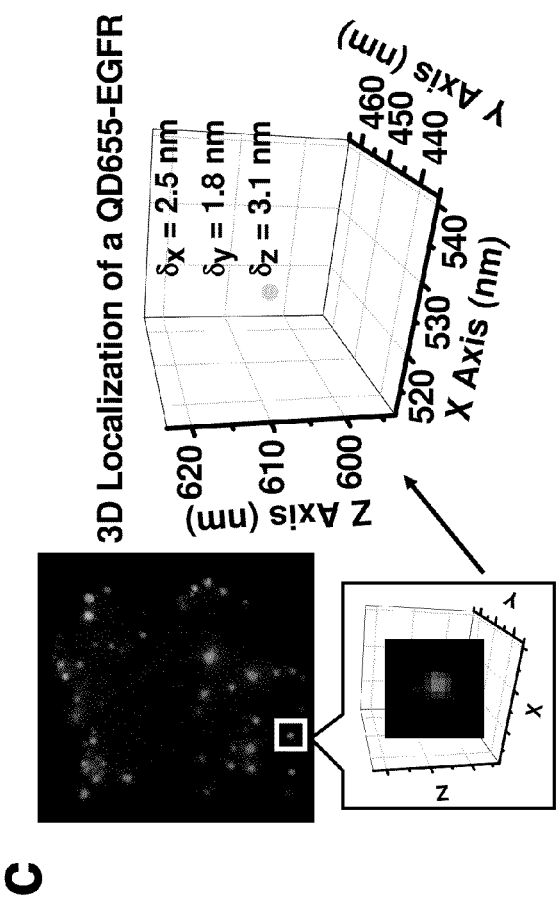
FIG. 4: 3D cell imaging by 2P holographic scan of QDs and 3D FIONA. (a) 2P images of live E. coli cells reveal helical stripes of QD (605 nm) labeled LamB receptor distribution on the cell membrane. 2P holographic matrix scan images yield better resolution than 1P widefield images. (b) Three dimensional (3D) FIONA fitting (bottom) of a 3D fluorescent spot localizes the center of it to 2~3 nm accuracy. Cross sections in three perpendicular planes passing the center of the spot are drawn. (c) A QD 655-labeled EGF receptor in a breast cancer cell localized in 3D, showing it is on the membrane of the cell. Average z accuracy is slightly lower than x and y accuracies.
Figure 5:
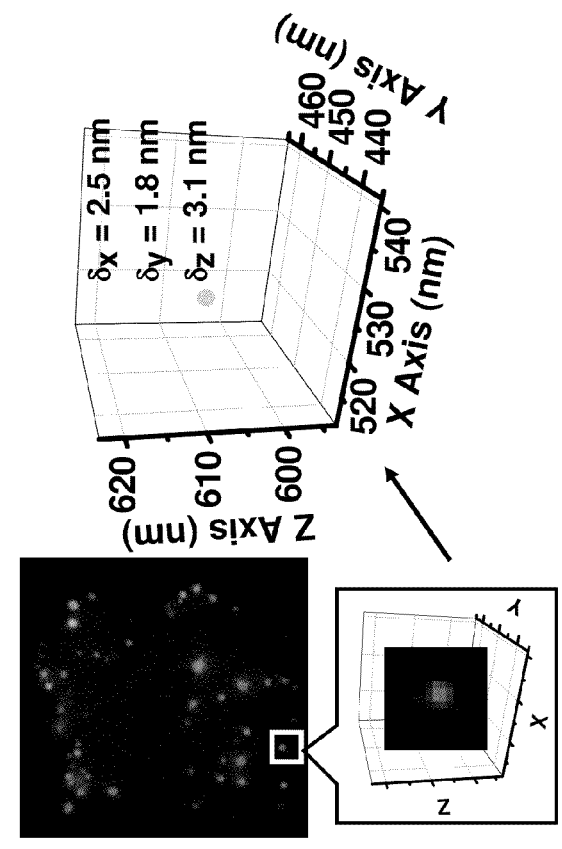
FIG. 5a, 5b: 3D FIONA of QD's by two photon matrix scan: 2P Matrix Excitation of Individual QDs and 3D FIONA of QDs by 2P Matrix Scan.
Figure 5:
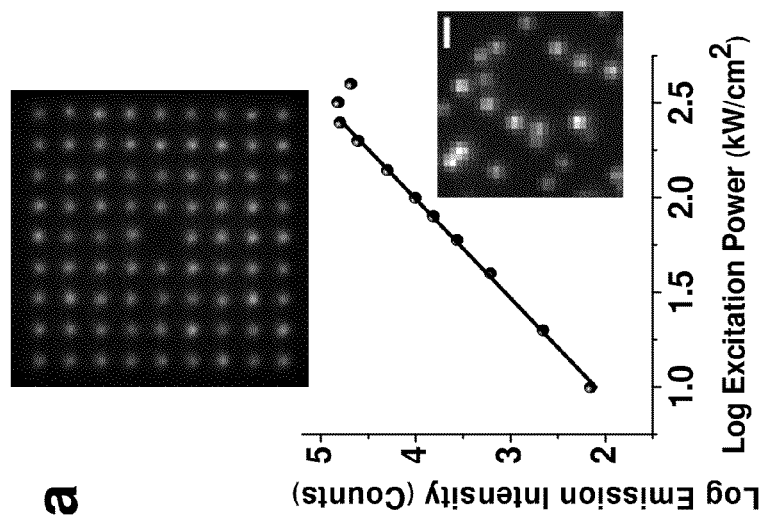

We are also able to produce 3-dimensional FIONA, instead of the usual 2-dimensional x-y FIONA. In part, this is because of the inherent confocality of scanning 2P excitation. In 2D FIONA, one takes a diffraction-limited spot in one image and fit it with a 2D Gaussian in the x-y plane. The accuracy of locating the center is determined by the equation derived by Thompson et al[20], approximately equal to the width of the Gaussian distribution divided by the square-root of the number of photons[10,20]. This yields nanometer accuracy in x and y. To get nanometer accuracy in the z-dimension, we took a series of x-y scan images along z; z-localization can then be determined by fitting x-z or y-z PSFs (which should yield the same value). Alternatively, a three-dimensional PSF can be constructed and the x, y and z positions can be resolved, as well as localization accuracies (FIG. 4b). We scanned every 100 nm in z so the effective pixelation in z was 100 nm, the same as in x and y.

Figure 6B:
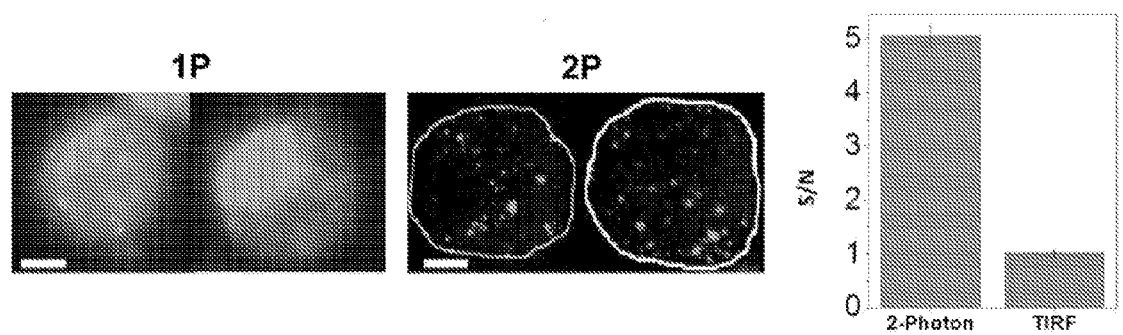
FIG. 6B. Comparison of the Signal to Noise (S/N) ratio of the same sample of breast cancer cells with EGFR labeled QDs, imaged using two excitation methods: 1P TIRF and 2P spot scanning.

As an example, we analyzed single QDs in a basal breast cancer cell line (MDA-MB-468) imaged with 2P in 3D with the holographic approach. The QDs are attached to the epidermal growth factor (EGF), and bound to ErbB1, its EGF-receptor (EGFR), which resides mostly at the plasma membrane of resting cells and is involved in cell proliferation. EGFR is a major drug target of for the treatment of various types of breast cancer. Mutations in EGFR have been found to be involved in unlicensed growth of malignant tumor cells[21-23]. If activated by EGF-treatment at 37° C. for 10-30 minutes, EGFRs are activated, followed by receptor endocytosis showing up under different z-slices[24]. We first treated the breast cancer cells with 4 nM QD605-EGF conjugates to trigger EGFR activation and internalization. Then we fixed the cells and mounted them with CyGEL. 1P imaged via TIR showed large autofluorescence (S/N=1), which was significantly reduced by 2P scanning (S/N=5) (FIG. 6B), in which individual QD-labeled EGFRs were clearly resolved (FIG. 4c, FIG. 6B). (It is therefore unlikely that a scanning-disk 1P-confocal microscope would reduce the autofluorescence enough to achieve the high signal-to-noise measured here with 2P microscopy.) Note that in FIG. 6B, for 1P TIRF imaging the QDs emission was masked by cells' membrane autofluorescence, while with 2P imaging QDs were clearly visible with minimal to no autofluorescence. S/N was calculated as the ratio of the mean intensity of observed QDs on the cell to the mean intensity of the whole cells, calculated for ten cells. A 3D image of an EGF-QD605 labeled breast cancer cell could be obtained within seconds (1~3s) for holographic imaging, or even sub-second, depending on the residence time on each pixel. In contrast, regular single-point scanning took one to a few minutes. The plotted data point in FIG. 4c shows the 3D position of a QD-labeled EGFR endosome in a representative breast cancer cell, localized at 2.5 nm, 1.8 nm and 3.1 nm accuracies in x, y and z, respectively. The z accuracy is slightly lower than x/y accuracies, which is expected because the PSF is slightly larger in the z dimension compared to the x-y dimension. Nevertheless, this indicates that we can achieve <3 nm accuracy in all three dimensions. As expected, the localization showed that receptors were internalized post EGF treatment. For EGFR dimer or oligomers, as they are smaller than the diffraction limit, we localize the center of the EGFR aggregation either on membrane or in cytoplasm.

In conclusion, we report two-photon excitation of individual QDs at room temperature in biological environments both in vitro and in vivo, and present a holographic type of scanning technique that improves the imaging rate by 80-fold. 3D nanometer localization accuracy can be obtained from the holographic scan data. The 2P-QD imaging system can easily integrate into conventional scan microscopy due to its simplicity and modularity. The technique provides a way to look inside live or fixed cells and tissues at single molecule level and nanometer resolution.

Materials and Methods: Flow chamber and in vitro QD samples: A glass slide (Fisher Scientific) with two holes was drilled at 1.5-2 cm separation. A glass coverslip (Fisher Scientific) with two strips of double-stick tape was added to form a flow chamber, followed by 5 Minute Epoxy (ITW Devcon) to seal the side of the flow chamber. 100 μL of 1 mg/mL BSA-biotin in pH 7.0 Phosphate Buffered Saline (PBS) buffer was flowed over the coverslip and allowed to sit for 10 min at room temperature (RT), and then washed with 60 μL PBS buffer. 100 μL of 100 pM QDs 525/565/585/605/655 nm, Invitrogen) in PBS buffer was flowed into the chamber and incubated at RT for 10 min. To photostabilize the QDs, 100 μL 100 mM DTT (or 10% 2-mercaptoethanol, or other reductants at various concentrations as tested in experiments) was flowed through the chamber to wash away non-immobilized QDs. Otherwise, PBS buffer was used.

E. coli cells: E. coli cells picked from a single colony on an agar plate were grown at 265 rpm rotation and 37° C. water bath overnight in 2 mL LB media in a 14 mL Falcon tube with 34 μg/mL antibiotics chloramphenicol. The next day 25 μL incubated cells were taken and added into 5 mL LB medium with antibiotics and 100 μM isopropyl-β-D-galactopyranoside (IPTG). It was then grown at 37° C. in water bath and 265 rpm rotation until the OD of the cell media reached 0.5-0.6. Cells were centrifuged in a 15 mL Eppendorf tube at 1000 rcf for 5 minutes, and the pellet was resuspended in 1 mL pH 7.0 PBS buffer. 100 μL of suspended E. coli cells in PBS buffer were then added to an appropriate volume of QD-streptavidin conjugates (Invitrogen), and they were incubated in RT for 10 min. Different kinds of QDs (525/565/605/655 nm or a combination) were selected as needed. 10 nM QDs were used to get dense labeling, while 1 nM or 100 pM were used to obtain single QD labeling. Labeled cells were centrifuged at 1000 rcf for 5 minutes and then washed by resuspending the pellet with 200 μL of pH 7.0 PBS buffer and repeated 3 to 5 times.

Breast cancer cells: MDA-MB-468 cells were cultured in L-15 medium (PAA, Farnborough, UK) supplemented with 10% fetal calf serum. Cells were plated onto sterile glass cover slips, fixed with 4% (w/v) paraformaldehyde for 15 min at RT before being treated with sodium borohydride (1 mg/mL in PBS, pH 7.4) to reduce free aldehyde groups, and blocked with 1% bovine serum albumin containing 100 nM streptavidin for 30 min at RT. Subsequently, cells were stained for 45 min at RT in the dark with 1 nM pre-formed EGF-QD complexes, which were prepared using EGF-biotin and a streptavidin-QD655 conjugate (both from Invitrogen, Paisley, UK) as described earlier[26]. Cells were washed five times with PBS before being mounted in CyGEL (Biostatus Limited, Leicestershire, UK).

Wide-field, and single-point scanning 2-photon microscope: The 2-photon widefield microscope was basically the same as a 1-photon widefield microscope, except a wavelength-tunable IR laser, Mai Tai HP (SpectraPhysics), was used as an excitation source instead of visible lasers (see SM1). Briefly, the microscope was based on an Olympus IX-71 inverted microscope. The laser was directed by dielectric mirrors (BB1-E03 and BB2-E03, Thorlabs) and focused by a 300 mm focus length (fl) lens (AR-coated at 650-1050 nm, Thorlabs) into the back aperture of a 100×1.45 numerical aperture (NA) achromatic objective (Olympus) and collimated through it. A 60×1.2 NA achromatic lens (Olympus) was also used for excitation beyond 900 nm due to its higher transparency to IR laser. For the single-point scanning setup, one 60 mm fl lens and one 300 mm fl lens (AR-coated at 650-1050 nm, Thorlabs) were used to expand and collimate the IR laser beam. The laser was focused to a diffraction limited excitation spot. A pair of motorized mirrors (ISS Inc., Champaign, Ill.) and a piezo stage (ISS) under the objective were used to scan the laser in x-y and z-axes, respectively; they were synchronized by an ISS dual clock module. The scan could run at various step sizes (typically at 50 nm, 64 nm or 100 nm), up to 100 µm scan range. A 725 nm short-pass or a 650 nm short-pass dichroic (Chroma) was used in the microscope. Emission filters such as HQ610/130M, HQ535/50M and ET750SP (Chroma) were selected according to QD emission spectra and inserted into the microscope to filter out excitation laser. For multicolor imaging, a QuadView tube or a DualView tube (Photometrics) was added after the microscope, and FF01-525/565/605/655/15-25 single band emission filters (Semrock) were included in the tube for the four colors of QDs. Images were recorded with an EM gain CCD camera (iXon+, Andor) or a Photomultiplier Tube (H7421-40, Hamamatsu).

Holographic matrix scanning microscope: The excitation laser spots were generated by a diffractive beam splitter, here called the Holographic Matrix (HM) (Holo/Or Ltd.). The HM was able to split the beam to be a 9×9 matrix with 0.09° separation. The line separation could be adjusted to 1.5 µm by adding an extra pair of 4f lenses with 0.4× magnification to the scanning beam path. The matrix scan shared the same beam path with the single-point scan, though the images could only be taken by EMCCD camera. Since the matrix scan is a kind of parallel scan, the scan mirrors need only to move over 1.5 µm×1.5 µm to cover a 13.5 µm×13.5 µm area, an 80-fold increase in imaging rate. The beam splitter worked optimally with 785 nm laser.

Matrix uniformity and calibration: The power distribution of excitation matrix spots is quite uniform, with the s.d. equal to 6%. The corresponding maximum fluorescence variation is ~14%. The effect of intensity variation on the accuracy of FIONA is negligible: since the localization accuracy is approximately proportional to the reciprocal of the square root of the total photon number, at most 14% of intensity variation would result in 6% variation of localization accuracy, i.e. 0.6 angstrom. Nevertheless, if correction is desired, we can calibrate the intensity by the fluorescence of the matrix on a dense and uniform film of QDs. Similar images are taken multiple times at different sample positions and averaged to diminish any effect of sample inhomogeneity. Intensities of fluorescent spots in the data images is then corrected by the normalized factors from the fluorescence intensity of each corresponding focal point of the matrix.

Excitation Spectra: We took widefield images of 1 µM QDs which densely covered the imaging area of the glass surface. The sample was made by dropping 4 µL 1 µM QD onto a glass slide and then clamped by an 18 mm×18 mm cover slip and sealed by 5 Minute Epoxy. We varied the excitation laser wavelength and recorded the excitation power and the emission intensity. To correct the excitation spectra, we obtained the emission intensity per unit excitation power by $Em0=Em/Ex2$, where the Em is the original emission intensity.

E. coli and breast cancer cells imaging. Labeled living E. coli cells were self-adhesive to the glass surface, and sealed between a coverslip and a slide. Fixed labeled breast cancer cells were mounted in CyGel and sealed between coverslip and slide. The samples were excited by a diffraction-limited excitation spot (single-point scan) or a multi-point HM scan. Laser power was tuned to ensure enough emission intensity while keeping excitation outside the diffraction limited spot to minimum. The scan range and step size were predetermined according to the need of the experiment, but most used scan step sizes were 50 nm, 64 nm, or 100 nm. Dwell time on each scan pixel was from 0.02 msec to 1 msec. Brightfield images of cells were also taken to show the profile of the whole cells.

Myosin V stepping assay and analysis: Myosin V was labeled on its cargo-binding domain with a 655 nm QD via anti-GFP antibody. F-Actin was polymerized at 1:20 biotinylation ratio (1 biotin/20 actin monomers) and immobilization onto glass coverslip surface via BSA-biotin-NeutrAvidin (Invitrogen) 9. Myosin V was then flowed into the sample chamber, excess myosin washed away, and a solution containing 1 µM ATP and 100 mM DTT was added. The sample was excited by 2-photon widefield, at 840 nm and 300 mW, and the fluorescence emission was imaged onto the EMCCD camera. The images were taken at 30 msec exposure time, 10 MHz readout rate, 5.2×pre-gain and 40 EM gain. With 250× total magnification (100× objective plus 2.5× additional tube lens), the effective pixel size was 64 nm. Detailed description about 2D-FIONA can be found in Yildiz et al.[9]. Localization accuracy is the standard error of the mean of the center of the Point Spread Function (PSF). The step size was determined by student's t-test.

3D FIONA data analysis: We obtain 3D FIONA either by 3D Gaussian fitting for the whole scan image PSF or by applying 2D Gaussian fitting in x-y image and virtual x-z/yz images. 3D Gaussian fitting is described in the article. Getting x-y location (x0, y0) with nanometer accuracy could also be done by applying standard 2D FIONA on the PSF in the brightest z slice. And, to accurately localize the z coordinate of the 3D spot via x-z or y-z PSF fitting, we established a virtual x-z plane by extracting intensities on all pixels at a constant y0. Similarly, a y-z PSF could be drawn. Moreover, we established a z-only one-dimensional PSF by extracting all z pixels at the constant point (x0, y0). Then we fit x-z and y-z PSF to 2D Gaussian, or z-only PSF to 1D Gaussian. Residuals of 3D and 2D Gaussian fitting were plotted and calculated. They showed the fittings to be excellent. All analysis was run by in-lab written programs in IDL or MatLab. Analysis of variance (ANOVA) showed no significant difference in the z localizations determined via the three kinds of PSFs above, as expected from theory.

References
1. Chan, W. C. W.; Nie, S. Science 1998, 281, (5385), 2016-2018.
2. Dahan, M.; Lévi, S.; Luccardini, C.; Rostaing, P.; Riveau, B.; Triller, A. Science 2003, 302, (5644), 442-445.
3. Michalet, X.; Pinaud, F. F.; Bentolila, L. A.; Tsay, J. M.; Doose, S.; Li, J. J.; Sundaresan, G.; Wu, A. M.; Gambhir, S. S.; Weiss, S. Science 2005, 307, (5709), 538-544.
4. Denk, W.; Strickler, J. H.; Webb, W. W. Science 1990, 248, (4951), 73-76.
5. Larson, D. R.; Zipfel, W. R.; Williams, R. M.; Clark, S. W.; Bruchez, M. P.; Wise, F. W.; Webb, W. W. Scicence 2003, 300, (5624), 1434-1436.
6. Rothenberg, E.; Ebenstein, Y.; Kazes, M.; Banin, U. J. Phys. Chem. B 2004, 108, (9), 2797-2800.
7. Verberk, R.; Oijen, A. M. v.; Orrit, M. Phys. Rev. B 2002, 66, (23), 233202.
8. Sanchez, E. J.; Novotny, L.; Holtom, G. R.; Xie, X. S. J. Phys. Chem. C 1997, 101, (38), 7019-7023.
9. Mertz, J.; Xu, C.; Webb, W. W. Opt. Lett. 1995, 20, (24), 2532-2534.

10. Yildiz, A.; Forkey, J. N.; McKinney, S. A.; Ha, T.; Goldman, Y. E.; Selvin, P. R. Science 2003, 300, 2601-2605.
11. Hohng, S.; Ha, T. J. Am. Chem. Soc. 2004, 126, (5), 1324-1325.
12. Mehta, A. D.; Rock, R. S.; Rief, M.; Spudich, J. A.; Mooseker, M. S.; Cheney, R. E. Nature 1999, 400, 590-593.
13. Kural, C.; Kim, H.; Syed, S.; Goshima, G.; Gelfand, V. I.; Selvin, P. R. Science 2005, 308, (5727), 1469-1472.
14. Tokunaga, M.; Imamoto, N.; Sakata-Sogawa, K. Nat. Methods 2008, 5, (2), 159-161.
15. Nielsen, T.; Fricke, M.; Hellweg, D.; Andresen, P. J. Microsc. 2001, 201, (3), 368-376.
16. Niesner, R.; Andresen, V.; Neumann, J.; Spiecker, H.; Gunzer, M. Biophys. J. 2007, 93, (7), 2519-2529.
17. Bewersdorf, J.; Pick, R.; Hell, S. W. Opt. Lett. 1998, 22, (9), 655-657.
18. Schwartz, M. Methods Enzymol. 1983, 97, 100-112.
19. Oddershede, L.; Dreyer, J. K.; Grego, S.; Brown, S.; Berg-Sørensen, K. Biophys. J. 2002, 83, (6), 3152-3161.
20. Thompson, R. E.; Larson, D. R.; Webb, W. W. Biophys. J. 2002, 82, (5), 2775-2783.
21. Lurje, G.; Lenz, H. J. Oncol. 2009, 77, 400-410.
22. Engelman, J. A.; Janne, P. A. Clin. Cancer Res. 2008, 14, (10), 2895-2899.
23. Ferguson, K. M. Annu. Rev. Biophys. 2008, 37, 353-373.
24. Sorkin, A.; Goh, L. K. Exp. Cell. Res. 2009, 315, 683-696.
25. (1) Xiao, M.; Phong, A.; Ha, C.; Chan, T.-F.; Cai, D.; Leung, L.; Wan, E.; Kistler, A. L.; DeRisi, J. L.; Selvin, P. R.; Kwok, P.-Y. Nucl. Acids Res. 2007, 35, e16-e16.
(26) Kartalov, E. P.; Unger, M. A.; Quake, S. R. BioTechniques 2003, 34, 505-510.
(27) Aitken, C. E.; Marshall, R. A.; Puglisi, J. D. Biophys J 2008, 94, 1826-1835.
(28) Rasnik, I.; McKinney, S. A.; Ha, T. Nat Meth 2006, 3, 891-893.
(29) Gordon, M. P.; Ha, T.; Selvin, P. R. Proceedings of the National Academy of Sciences of the United States of America 2004, 101, 6462-6465.
(30) Goshtasby, A. Image Vision Comput. 1988, 6, 255-261.
(31) Goshtasby, A. Pattern Recognition 1986, 19, 459-466.

Unless otherwise explained, all technical and scientific terms used herein have the same meaning as commonly understood by one of ordinary skill in the art to which a disclosed disclosure belongs. The singular terms "a," "an," and "the" include plural referents unless context clearly indicates otherwise. Similarly, the word "or" is intended to include "and" unless the context clearly indicates otherwise. All references cited herein are incorporated by reference.

While the present disclosure can take many different forms, for the purpose of promoting an understanding of the principles of the disclosure, reference will now be made to the embodiments illustrated in the drawings and specific language will be used to describe the same. It will nevertheless be understood that no limitation of the scope of the disclosure is thereby intended. Any alterations and further modifications of the described embodiments, and any further applications of the principles of the disclosure as described herein are contemplated as would normally occur to one skilled in the art to which the disclosure relates.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure. Thus, it should be understood that although the present disclosure has been specifically disclosed by preferred embodiments, exemplary embodiments and optional features, modification and variation of the concepts herein disclosed may be resorted to by those skilled in the art, and that such modifications and variations are considered to be within the scope of this disclosure as defined by the appended aspects. The specific embodiments provided herein are examples of useful embodiments of the present disclosure and it will be apparent to one skilled in the art that the present disclosure may be carried out using a large number of variations of the devices, device components, methods steps set forth in the present description. As will be obvious to one of skill in the art, methods and devices useful for the present methods can include a large number of optional composition and processing elements and steps.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the aspects herein.

All patents and publications mentioned in the specification are indicative of the levels of skill of those skilled in the art to which the disclosure pertains. References cited herein are incorporated by reference herein in their entirety to indicate the state of the art as of their publication or filing date and it is intended that this information can be employed herein, if needed, to exclude specific embodiments that are in the prior art. For example, when compositions of matter are disclosed, it should be understood that compounds known and available in the art prior to Applicant's disclosure, including compounds for which an enabling disclosure is provided in the references cited herein, are not intended to be included in the composition of matter aspects herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the aspect element. As used herein, "consisting essentially of" does not exclude materials or steps that do not materially affect the basic and novel characteristics of the aspect. In each instance herein any of the terms "comprising", "consisting essentially of" and "consisting of" may be replaced with either of the other two terms. The disclosure illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the disclosure without resort to undue experimentation. All art-known functional equivalents, of any such materials and methods are intended to be included in this disclosure. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by the appended aspects.

Although the present disclosure has been described with reference to certain embodiments thereof, other embodiments are possible without departing from the present disclosure. The spirit and scope of the appended aspects should not be limited, therefore, to the description of the preferred embodiments contained herein. All embodiments that come within the meaning of the aspects, either literally or by equivalence, are intended to be embraced therein. Furthermore, the advantages described above are not necessarily the only advantages of the disclosure, and it is not necessarily expected that all of the described advantages will be achieved with every embodiment of the disclosure.

What is claimed is:

1. A method of microscopy comprising the step of imaging individual quantum dots (QD) using two-photon (2P) microscopy in an aqueous environment with widefield and point-scan excitations at nanometer accuracy.

2. The method of claim 1 further comprising the step of using a thiol-containing reductant to suppress QD blinking.

3. The method of claim 1 further comprising the step of localizing the QDs with an accuracy of 2~3 nm in all three dimensions by using a 9×9 matrix excitation hologram and an array detector 4. The method of claim 1 further comprising the step of using a holographic matrix in excitation and an electron multiplying charge coupled device (EMCCD) in detection.

5. The method of claim 1 wherein the imaging is performed at ambient (room) or cell-viability permissive temperature.

6. The method of claim 1 wherein the quantum dots are attached to a biological molecule, wherein the method images the molecule, wherein the molecule is present on or in a cell.

7. The method of claim 1 further comprising the steps of:
using a thiol-containing reductant to suppress QD blinking;
localizing the QDs with an accuracy of 2~3 nm in all three dimensions by using a 9×9 matrix excitation hologram and an array detector; and
using a holographic matrix in excitation and an electron multiplying charge coupled device (EMCCD) in detection.

8. The method of claim 7 wherein the imaging is performed at ambient (room) or cell-viability permissive temperature.

9. The method of claim 7 wherein the quantum dots are attached to a biological molecule, wherein the method images the molecule, wherein the molecule is present on or in a cell.

10. An imaging system specifically adapted for implementing the method of claim 1 of imaging individual quantum dots (QD) using two-photon (2P) microscopy in an aqueous environment with wide-field and point-scan excitations at nanometer accuracy and comprising the components and arrangements as follows: a sample chamber, objective, a piezo stage, a CCD camera or photomultiplier tube (PMT), an IR laser, mirrors and lenses, configured so that light from the laser is directed by mirrors and focused by a lens into the back aperture of the objective and collimated through it to the sample chamber, mirrors and the piezo stage are under the objective scan the laser in x-y and z-axes, and images are transmitted to and recorded with the CCD camera or PMT.

* * * * *